US012697291B2

(12) United States Patent
Roudot et al.

(10) Patent No.: US 12,697,291 B2
(45) Date of Patent: Aug. 4, 2026

(54) COSMETIC COMPOSITION COMPRISING WATER-SOLUBLE OR WATER-DISPERSIBLE UV-SCREENING AGENTS, HYDROPHILIC THICKENERS AND HYDROPHILIC SURFACTANTS

(71) Applicant: L'OREAL, Paris (FR)

(72) Inventors: Angélina Roudot, Chevilly la Rue (FR); Laure Ader, Chevilly la Rue (FR); Flavie Gillant, Chevilly la Rue (FR)

(73) Assignee: L'OREAL, Paris (FR)

( * ) Notice: Subject to any disclaimer, the term of this patent is extended or adjusted under 35 U.S.C. 154(b) by 1050 days.

(21) Appl. No.: 17/783,804

(22) PCT Filed: Dec. 3, 2020

(86) PCT No.: PCT/EP2020/084509
§ 371 (c)(1),
(2) Date: Jun. 9, 2022

(87) PCT Pub. No.: WO2021/122041
PCT Pub. Date: Jun. 24, 2021

(65) Prior Publication Data

US 2023/0028965 A1 Jan. 26, 2023

(30) Foreign Application Priority Data

Dec. 17, 2019 (FR) ...................................... 1914678

(51) Int. Cl.

| | |
|---|---|
| ***A61K 8/49*** | (2006.01) |
| ***A61K 8/06*** | (2006.01) |
| ***A61K 8/46*** | (2006.01) |
| ***A61K 8/73*** | (2006.01) |
| ***A61K 8/81*** | (2006.01) |
| ***A61Q 17/04*** | (2006.01) |

(52) U.S. Cl.
CPC ............ *A61K 8/4946* (2013.01); *A61K 8/062* (2013.01); *A61K 8/466* (2013.01); *A61K 8/73* (2013.01); *A61K 8/8147* (2013.01); *A61Q 17/04* (2013.01); *A61K 2800/48* (2013.01)

(58) Field of Classification Search
None
See application file for complete search history.

(56) References Cited

U.S. PATENT DOCUMENTS

2011/0152384 A1* 6/2011 Gunn ........................ A61K 8/73
514/784

FOREIGN PATENT DOCUMENTS

| | | | | | |
|---|---|---|---|---|---|
| EP | 1570836 | A1 | | 9/2005 | |
| FR | 2970172 | A1 | | 7/2012 | |
| WO | 2012130606 | A1 | | 10/2012 | |
| WO | WO-2016008117 | A1 | * | 1/2016 | ........... A61K 8/8152 |
| WO | WO-2016166345 | A1 | * | 10/2016 | .............. A61P 17/18 |

OTHER PUBLICATIONS

English language translation of WO 2016/166345 A1. (Year: 2016).*
International Search Report and Written Opinion issued on Feb. 1, 2021 for corresponding PCT Application No. PCT/EP2020/084509.
International Preliminary Report on Patentability issued on May 17, 2022 for corresponding PCT Application No. PCT/EP2020/084509.
Anonymous: "Personal Care compositions comprising UV filters in combination with Keratin Binding Polypeptides," ip.com Journal, 2005, pp. 1-63 XP013112208.

* cited by examiner

*Primary Examiner* — Dominic Lazaro
(74) *Attorney, Agent, or Firm* — POLSINELLI PC

(57) ABSTRACT

The present invention relates to a composition, notably an aqueous cosmetic composition, comprising at least one screening agent chosen from water-soluble or water-dispersible screening agents that are capable of absorbing UV rays from 320 to 400 nm (UVA), water-soluble or water-dispersible screening agents that are capable of absorbing UV rays from 280 to 320 nm (UVB), and mixtures thereof; at least one hydrophilic thickener; and at least one surfactant with an HLB of greater than or equal to 7.

The present invention also relates to a non-therapeutic cosmetic process for treating keratin materials, preferably the skin, comprising the application, to said keratin materials, of a composition according to the invention.

29 Claims, No Drawings

COSMETIC COMPOSITION COMPRISING WATER-SOLUBLE OR WATER-DISPERSIBLE UV-SCREENING AGENTS, HYDROPHILIC THICKENERS AND HYDROPHILIC SURFACTANTS

CROSS REFERENCE TO RELATED APPLICATIONS

This application is a National Phase filing under 35 U.S.C. § 371 of PCT/EP2020/084509 filed on 3 Dec. 2020; which application in turn claims priority to Application No. 1914678 filed in France on 17 Dec. 2019. The entire contents of each application are hereby incorporated by reference.

The present invention relates to a composition, notably an aqueous cosmetic composition, comprising at least one screening agent chosen from water-soluble or water-dispersible screening agents that are capable of absorbing UV rays from 320 to 400 nm (UVA), water-soluble or water-dispersible screening agents that are capable of absorbing UV rays from 280 to 320 nm (UVB), and mixtures thereof; at least one hydrophilic thickener; and at least one surfactant with an HLB of greater than or equal to 7.

It is known that radiation with wavelengths of between 280 nm and 400 nm allows tanning of the human epidermis, whereas radiation with wavelengths of between 280 and 320 nm, known as UVB rays, harms the development of a natural tan. Exposure is also liable to bring about a detrimental change in the biomechanical properties of the epidermis, which is reflected by the appearance of wrinkles, leading to premature ageing of the skin.

It is also known that UVA rays, with a wavelength of between 320 and 400 nm, penetrate more deeply into the skin than UVB rays. UVA rays bring about immediate and persistent tanning of the skin. Under normal conditions, daily exposure to UVA rays, even of short duration, can damage the collagen fibres and the elastin, which is reflected by a change in the microrelief of the skin, the appearance of wrinkles and uneven pigmentation (spots, lack of uniformity of the complexion).

A wide variety of photoprotective compositions are already known to date for protecting keratin materials, and more particularly the skin, against the harmful effects induced by UVA and/or UVB radiation. They mostly contain a combination of several organic or inorganic UV-screening agents, conveyed in an oily phase and/or in an aqueous phase as anti-UV active agent and are generally proposed in a presentation form of emulsion or gel type.

It is also known that high contents of screening agents are required to achieve high levels of screening efficiency.

However, high contents of UV-screening agents do not lend themselves to easy production of compositions having a stabilized and pleasant texture.

Thus, formulations with high screening power generally have uncomfortable or even unpleasant sensory aspects masking the freshness and comfort of the formulations. In particular, the weak point of photoprotective formulations with a high protection factor is often a strong greasy feel, and thus a lack of lightness of the textures obtained, but also a white appearance on application, thus not being invisible on the skin.

Moreover, the introduction of a high content of UV-screening agents generally brings about destabilization problems. This instability may even occasionally cause phase separation of the emulsion and/or a loss of viscosity of the composition, making the formulation inefficient or even unusable.

To overcome the abovementioned undesirable effects, and in particular to obtain a fresh effect on application and an invisible effect on the skin, aqueous presentation forms have already been considered. However, these aqueous compositions containing UV-screening agents are generally tacky and thus uncomfortable.

Consequently, there is a need for an aqueous photoprotective composition with a high level of UV protection, which is perfectly stable and homogeneous, i.e. not subject to demixing.

There is still a need for an aqueous photoprotective composition with a high level of UV protection which is moreover transparent. Furthermore, there is a need for a photoprotective composition that is transparent even after application to the skin.

There is also still a need for an aqueous photoprotective composition with a high level of UV protection, which has good cosmetic properties on application, notably which is easy to apply, without a greasy or tacky finish on the skin, in particular after drying, and which has a pleasant sensory effect in particular materialized by glidance on application.

The object of the present invention is to propose novel cosmetic compositions that overcome these problems.

In particular, the object of the present invention is to propose novel compositions, notably aqueous cosmetic compositions, comprising water-soluble or water-dispersible UV-screening agents, which are stable and homogeneous.

One subject of the present invention is thus a composition, notably an aqueous cosmetic composition, comprising at least one screening agent chosen from water-soluble or water-dispersible screening agents that are capable of absorbing UV rays from 320 to 400 nm (UVA), water-soluble or water-dispersible screening agents that are capable of absorbing UV rays from 280 to 320 nm (UVB), and mixtures thereof; at least one hydrophilic thickener; and at least one surfactant with an HLB of greater than or equal to 7.

The composition according to the invention is intended for topical application and thus contains a physiologically acceptable medium. The term "physiologically acceptable medium" means here a medium that is compatible with keratin materials.

In the context of the present invention, the term "keratin material" notably means the skin (of the body, face, around the eyes, or the eyelids), the scalp, keratin fibres such as the eyelashes, the eyebrows, head hair, bodily hair, the nails, and mucous membranes such as the lips, and more particularly the skin, notably bodily and/or facial skin.

The composition in accordance with the invention is aqueous. For the purposes of the present invention, the term "aqueous" refers to a composition having an amount of fatty phase of less than 10% by weight, preferably less than 5% by weight and even more preferentially less than 2% by weight relative to the weight of the composition. Advantageously, the composition in accordance with the invention is essentially aqueous, i.e. it does not contain a fatty phase.

By virtue of the presence of one or more hydrophilic thickeners, the compositions according to the invention make it possible to achieve a wide variety of textures, i.e. from fluid to very viscous solutions.

These compositions are stable over time and homogeneous.

According to the present invention, the term "stable over time" refers to a composition which, after one month, preferably after two months, of storage at a temperature ranging from 4° C. to 45° C., does not show any macroscopic change in colour, odour or viscosity, or any variation in pH, and also no variation in microscopic appearance.

The term "homogeneous" means that the composition is in the form of a single phase, without grains in suspension in the composition or on the walls of the container that are visible to the naked eye, and/or that it has a uniform texture, i.e. without any pieces of gel in solution.

According to a particular embodiment, the composition of the present invention is transparent or translucent. According to certain preferred embodiments, the composition according to the invention is a transparent composition.

For the purposes of the present invention, the term "transparent or translucent composition" refers to a composition which has a turbidity value of less than 1000 NTU, preferably less than 800 NTU, even more preferentially less than 500 NTU, better still less than 200 NTU, preferably less than 150 NTU, notably less than 100 NTU. Preferably, the turbidity of the compositions is at least equal to 1 NTU.

The NTU (nephelometric turbidity unit) is the unit for measuring the turbidity of a composition. The turbidity measurement is performed, for example, with a 2100P model turbidimeter from the Hach Company, the tubes used for the measurement being referenced AR397A cat 24347-06. The measurements are performed at room temperature (from 20° C. to 25° C.).

Preferably, the composition is transparent and has a turbidity value of between 1 and 200 NTU, preferably between 1 and 150 NTU, preferably less than 100 NTU.

Preferably, the composition is transparent after it has been applied to the skin, i.e. no white marks are left after spreading the composition on the skin.

A subject of the present invention is also a non-therapeutic cosmetic process for treating keratin materials, preferably the skin, comprising the application, to said keratin materials, of a composition according to the invention.

In the text hereinbelow, unless otherwise indicated, the limits of a range of values are included in that range, notably in the expressions "between" and "ranging from . . . to . . . ".

Moreover, the expressions "at least one" and "at least" used in the present description are equivalent to the expressions "one or more" and "greater than or equal to", respectively.

Water-Soluble and Water-Dispersible Screening Agents

The composition according to the invention comprises at least one screening agent chosen from water-soluble or water-dispersible screening agents that are capable of absorbing UV rays from 320 to 400 nm (UVA), water-soluble or water-dispersible screening agents that are capable of absorbing UV rays from 280 to 320 nm (UVB), and mixtures thereof.

According to a particular embodiment, the composition according to the invention comprises at least one screening agent chosen from water-soluble screening agents that are capable of absorbing UV rays from 320 to 400 nm (UVA), water-soluble screening agents that are capable of absorbing UV rays from 280 to 320 nm (UVB), and mixtures thereof.

According to another particular embodiment, the composition in accordance with the invention comprises at least one water-soluble or water-dispersible screening agent that is capable of absorbing UVA rays and at least one water-soluble or water-dispersible screening agent that is capable of absorbing UVB rays.

Preferably, the composition in accordance with the invention comprises at least one water-soluble screening agent that is capable of absorbing UVA rays and at least one water-soluble screening agent that is capable of absorbing UVB rays.

The term "water-soluble screening agent" means any mineral or organic screening agent that can be fully dissolved in molecular form in a liquid aqueous phase or that can be dissolved in colloidal form (for example in micellar form) in a liquid aqueous phase.

The term "water-dispersible screening agent" means any mineral or organic screening agent that is capable of forming, in a liquid aqueous phase, a homogeneous suspension of particles of less than 100 microns.

According to a particular embodiment, the screening agent(s) present in the composition in accordance with the invention are chosen from water-soluble organic screening agents.

Among the water-soluble organic UVA-screening agents that may be used according to the present invention, mention may be made of benzene-1,4-bis(3-methylidene-10-camphorsulfonic) acid (INCI name: Terephthalylidene Dicamphor Sulfonic Acid) and the various salts thereof, notably described in patent applications FR-A-2528420 and FR-A-2639347. Mention may notably be made of benzene-1,4-bis(3-methylidene-10-camphorsulfonic acid) (INCI name: Terephthalylidene Dicamphor Sulfonic Acid) such as the product which is manufactured under the name Mexoryl SX by Chimex.

These screening agents correspond to general formula (I) below:

(I)

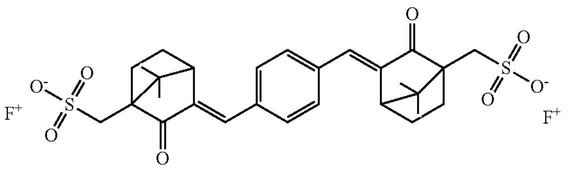

in which F denotes a hydrogen atom, an alkali metal or a radical $NH(R_1)_3^+$ in which the radicals $R_1$, which may be identical or different, denote a hydrogen atom, a $C_1$ to $C_4$ alkyl or hydroxyalkyl radical or a group $Mn^+$, $Mn^+$ denoting a polyvalent metal cation in which n is equal to 2 or 3 or 4, $Mn^+$ preferably denoting a metal cation chosen from $Ca^{2+}$, $Zn^{2+}$, $Mg^{2+}$, $Ba^{2+}$, $Al^{3+}$ and $Zr^{4+}$. It is clearly understood that the compounds of formula (I) above can give rise to the "cis-trans" isomer around one or more double bonds and that all the isomers fall within the context of the present invention.

Among the hydrophilic organic UVA-screening agents that may be used according to the present invention, mention may also be made of compounds including at least two benzazolyl groups bearing sulfonic groups, such as those described in patent application EP-A-0669323.

They are described and prepared according to the syntheses indicated in U.S. Pat. No. 2,463,264 and also in patent application EP-A-0669323.

The compounds including at least two benzazolyl groups in accordance with the invention correspond to the general formula (11) below:

(II)

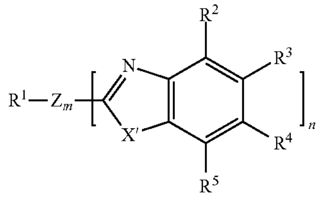

in which:

Z represents an organic residue of valency (l+n) including one or more double bonds placed such that it completes the system of double bonds of at least two benzazolyl groups as defined inside the square brackets so as to form a fully conjugated assembly;

X denotes S, O or $NR^6$;

$R^1$ denotes a hydrogen atom, a $C_1$ to $C_{18}$ alkyl, a $C_1$ to $C_4$ alkoxy, a $C_5$ to $C_{15}$ aryl, a $C_2$ to $C_{18}$ acyloxy, or a group $SO_3Y$ or COOY;

the radicals $R^2$, $R^3$, $R^4$ and $R^5$, which may be identical or different, denote a nitro group or a radical $R^1$;

$R^6$ denotes a hydrogen atom, a $C_1$ to $C_4$ alkyl or a $C_1$ to $C_4$ hydroxyalkyl;

Y denotes a hydrogen atom, Li, Na, K, $NH_4$, ½Ca, ½Mg, ⅓Al or a cation resulting from the neutralization of a free acid group with an organonitrogen base;

m is 0 or 1;

n is a number from 2 to 6;

l is a number from 1 to 4;

with the proviso that 1+n does not exceed the value 6.

Among all these compounds, preference will most particularly be given to 1,4-bis(benzimidazolyl)phenylene-3,3',5,5'-tetrasulfonic acid (INCI name: Disodium Phenyl Dibenzimidazole Tetrasulfonate) or a salt thereof, having the following structure, notably sold under the name Neoheliopan AP® by the company Haarmann and Reimer:

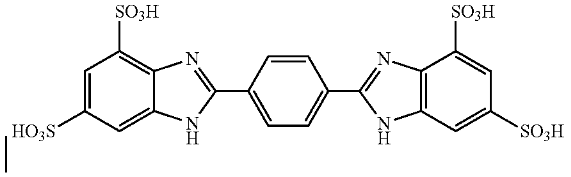

Preferably, the water-soluble screening agent that is capable of absorbing UVA rays is benzene-1,4-bis(3-methylidene-10-camphorsulfonic acid) (INCI name: Terephthalylidene Dicamphor Sulfonic Acid) such as the product which is manufactured under the name Mexoryl SX by Chimex.

The water-soluble organic UVB-screening agents that may be used according to the present invention are notably chosen from water-soluble cinnamic derivatives, such as ferulic acid or 3-methoxy-4-hydroxycinnamic acid; water-soluble benzylidenecamphor compounds; water-soluble phenylbenzimidazole compounds; water-soluble p-aminobenzoic (PABA) compounds; water-soluble salicylic compounds, and mixtures thereof.

As examples of water-soluble organic UVB-screening agents, mention may be made of the following compounds denoted under their INCI name:

para-aminobenzoic compounds, such as PABA, Glyceryl PABA or PEG-25 PABA notably sold under the name Uvinul P 25® by BASF;

cinnamic derivatives such as ferulic acid or DEA methoxycinnamate;

salicylic compounds, such as dipropylene glycol salicylate notably sold under the name Dipsal® by Scher, and TEA salicylate, notably sold under the name Neo Heliopan TS® by Symrise;

benzylidenecamphor compounds, such as benzylidenecamphorsulfonic acid notably sold under the name Mexoryl SL® by Chimex, and camphor benzalkonium methosulfate notably sold under the name Mexoryl SO® by Chimex;

phenylbenzimidazole compounds, such as 2-phenyl-1H-benzimidazole-5-sulfonic acid (INCI name: phenylbenzimidazole sulfonic acid) notably sold under the trade name Eusolex 232® by Merck.

Use will more particularly be made of 2-phenyl-1H-benzimidazole-5-sulfonic acid (INCI name: phenylbenzimidazole sulfonic acid) notably sold under the trade name Eusolex 232® by Merck.

The composition according to the invention may also comprise at least one mixed water-soluble screening agent that is capable of absorbing UVA and UVB rays, among which mention may notably be made of benzophenone compounds comprising at least one sulfonic acid function, for instance the following compounds:

Benzophenone-4, notably sold by the company BASF under the name Uvinul MS40®:

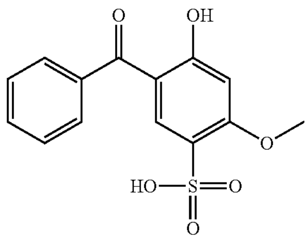

,

Benzophenone-5 having the structure

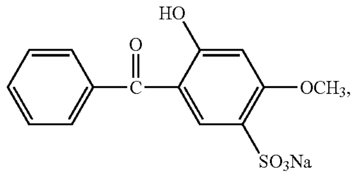

Benzophenone-9, notably sold by the company BASF under the name Uvinul DS49®:

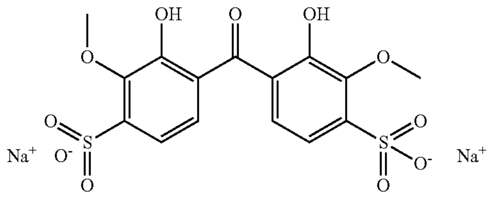

,

Preferably, the composition according to the invention comprises a total amount of water-soluble or water-dispersible screening agents of between 0.2% and 40% by weight, preferably between 0.5% 40% by weight, even more preferentially between 1% and 30% by weight, better still between 2% and 25% by weight, and even more preferably between 3% and 20% by weight, relative to the total weight of the composition.

According to a particular embodiment, the composition in accordance with the invention comprises one or more water-soluble screening agents that are capable of absorbing UVA rays, in an amount of between 0.2% and 40% by weight, preferably between 0.5% and 30% by weight, relative to the total weight of the composition, preferably between 1% and 20% by weight, better still between 1.5% and 15% by weight, and even more preferentially between 2% and 10% by weight.

According to another particular embodiment, the composition in accordance with the invention comprises one or more water-soluble screening agents that are capable of absorbing UVB rays, in an amount of between 0.2% and 40% by weight, preferably between 0.5% and 30% by weight, preferably between 1% and 20% by weight, preferably between 1.5% and 10% by weight relative to the total weight of the composition.

When the water-soluble UV-screening agent is of sulfonic acid type, it is preferably associated with an organic base, such as an alkanolamine.

The term "alkanolamine" means a C2-C10 compound comprising at least one primary, secondary or tertiary amine function and at least one alcohol function, generally a primary alcohol function. As suitable alkanolamines, mention may be made of 2-amino-2-(hydroxymethyl)-1,3-propanediol (INCI name: Tromethamine) and triethanolamine.

Hydrophilic Gelling Agents

The composition according to the invention comprises at least one hydrophilic gelling agent (or hydrophilic thickener).

For the purposes of the present invention, the term "hydrophilic gelling agent" (or hydrophilic thickener) means a compound that is capable of gelling the aqueous phase of the compositions according to the invention.

In particular, in the context of the present patent application, the term "thickener" notably means an agent for increasing at least 10-fold, preferably at least 15-fold, preferably at least 20-fold, the viscosity of a mixture comprising said agent at 1% by weight, triethanolamine at 0.9% by weight and water, at a temperature of 25° C.

According to a particular embodiment of the invention, the hydrophilic gelling agent(s) are polymeric.

The hydrophilic gelling agent(s) may be chosen from anionic synthetic thickening polymers, nonionic thickening polysaccharides, sulfate-based thickening polysaccharides and carboxylic branched thickening polysaccharides.

The term "carboxylic" means comprising at least one carboxylic acid function.

Preferably, the composition according to the invention is substantially free (i.e. contains less than 0.4%, preferably less than 0.3%, preferably less than 0.2% and better still less than 0.1% by weight relative to the total weight of the composition), and is preferably totally free, of thickener chosen from clays, mica, modified starches such as phosphate starches, and gellan gum.

Anionic Synthetic Thickening Polymers

The composition according to the invention may comprise an anionic synthetic thickening polymer.

Preferably, the anionic synthetic thickening polymer is non-aromatic; this means that it does not contain any aromatic monomers.

Among the anionic synthetic thickening polymers that may be used, mention may be made of crosslinked homopolymers or copolymers of acrylic or methacrylic acid, crosslinked or non-crosslinked 2-acrylamido-2-methylpropanesulfonic acid homopolymers, or salts thereof, and copolymers of acrylamido-2-methylpropanesulfonic acid or salts thereof and of one or more crosslinked or non-crosslinked nonionic monomers, alone or as mixtures.

A first family of thickening polymers that is suitable for use is represented by crosslinked acrylic acid homopolymers. Among the homopolymers of this type, mention may be made of those crosslinked with an allyl alcohol ether of the sugar series, such as, for example, the products sold under the names Carbopol 980, 981, 954, 2984 and 5984 by the company Lubrizol or the products sold under the names Synthalen M and Synthalen K by the company 3V.

Such acrylic homopolymers may be present in the composition in a particulate or non-particulate form. When they are present in a particulate form, their mean size in the hydrated state is preferably less than or equal to 10 μm and even more preferentially less than or equal to 5 μm. Their mean size in the non-hydrated state is preferably less than or equal to 2 μm, preferably less than or equal to 1 μm.

Preferably, the acrylic acid homopolymer is present in non-particulate form.

Preferably, use is made of an at least partially neutralized acrylic acid homopolymer. The homopolymer used according to the invention is chosen in particular from sodium polyacrylates and potassium polyacrylates. Sodium polyacrylate is preferably used.

As regards these acrylic polymers already neutralized before use, examples that may be mentioned include:

- sodium polyacrylates such as those sold under the name Cosmedia SP® containing 90% dry material and 10% water, or Cosmedia SPL® as an inverse emulsion containing about 60% dry active material, an oil (hydrogenated polydecene) and a surfactant (PPG-5 laureth-5), both sold by the company BASF;
- partially neutralized sodium polyacrylates, notably in the form of an inverse emulsion comprising at least one polar oil, for example the product sold under the name Luvigel® EM sold by the company BASF; and
- mixtures thereof.

Use may also be made of an acrylic acid polymer that is not neutralized beforehand, which is then partially or totally neutralized before use by any suitable means and notably by adding any base such as sodium hydroxide, potassium hydroxide or an alkanolamine such as triethanolamine. Sodium polyacrylates are thus notably obtained. Potassium polyacrylates are also suitable for use in the present invention.

A second family of thickening polymers that is suitable for use is represented by crosslinked copolymers of (meth) acrylic acid and of a C1-C30 alkyl acrylate.

Preferably, these copolymers are crosslinked copolymers of (meth)acrylic acid and of a C1-C6 alkyl acrylate.

The (meth)acrylic acid monomer is preferably present in amounts ranging from 20% to 80% by weight, more particularly from 25% to 70% by weight and even more particularly from 35% to 60% by weight relative to the total weight of the copolymer.

The C1-C6 alkyl acrylate monomer is preferably present in amounts ranging from 15% to 80% by weight, more particularly from 25% to 75% by weight and even more particularly from 40% to 65% by weight relative to the total weight of the copolymer. Among these monomers, mention may be made of methyl acrylate, ethyl acrylate, n-butyl acrylate, 2-hydroxyethyl acrylate, styrene, acrylamide, N,N- dimethylacrylamide, tert-butylacrylamide, methyl methacrylate, ethyl methacrylate, n-butyl methacrylate and 2-hydroxyethyl methacrylate.

Such a copolymer is typically partially or totally crosslinked with at least one conventional crosslinking agent. The crosslinking agents are notably polyunsaturated compounds. These compounds are notably polyalkenyl ethers of sucrose or of polyols, diallyl phthalates, divinylbenzene, allyl (meth)acrylate, ethylene glycol di(meth)acrylate, methylenebisacrylamide, trimethylolpropane tri(meth)acrylate, diallyl itaconate, diallyl fumarate, diallyl maleate, zinc (meth)acrylate, and castor oil or polyol derivatives manufactured from unsaturated carboxylic acids. As crosslinking agent, use may also be made of unsaturated monomeric compounds including a reactive group that is capable of reacting with an unsaturation to form a crosslinked copolymer. The content of crosslinking agent generally ranges from 0.01% to 5% by weight, preferably from 0.03% to 3% by weight and even more particularly from 0.05% to 1% by weight relative to the total weight of the copolymer.

The preferred crosslinked copolymer of (meth)acrylic acid and of a C1-C6 alkyl acrylate according to the invention is chosen from crosslinked copolymers of methacrylic acid and of a C1-C6 alkyl acrylate, crosslinked copolymers of acrylic acid and of a C1-C6 alkyl acrylate, and more particularly a crosslinked copolymer of methacrylic acid and of ethyl acrylate.

According to a particularly preferred form, the copolymer of the invention may notably be in the form of a dispersion in water. The number-average size of the copolymer particles in the dispersion is generally between 10 and 500 nm, preferably between 20 and 200 nm and more preferentially from 50 to 150 nm.

Among the crosslinked copolymers of (meth)acrylic acid and of a C1-C6 alkyl acrylate, mention may be made of the product sold under the name Viscoatex 538C by the company Coatex, which is a crosslinked copolymer of (meth)acrylic acid and of C1-C4 alkyl acrylate (in particular ethyl acrylate) as an aqueous dispersion containing 38% active material, or the product sold under the name Aculyn 33 by the company Röhm & Haas, which is a crosslinked copolymer of acrylic acid and of ethyl acrylate as an aqueous dispersion containing 28% active material. Mention may more particularly be made of the crosslinked methacrylic acid/ethyl acrylate copolymer in the form of an aqueous 30% dispersion manufactured and sold under the name Carbopol Aqua SF-1 by the company Lubrizol.

A third family of suitable thickening polymers is represented by crosslinked or non-crosslinked 2-acrylamido-2-methylpropanesulfonic acid (AMPS®) homopolymers, or salts thereof. These homopolymers may be crosslinked or non-crosslinked.

Such a homopolymer may have a number-average molecular weight ranging from 1000 to 20 000 000 g/mol, preferably ranging from 20 000 to 5 000 000 and even more preferentially from 100 000 to 1 500 000 g/mol.

More particularly, use is made of 2-acrylamido-2-methylpropanesulfonic acid, and also partially or totally neutralized forms thereof.

When the polymers are crosslinked, the crosslinking agents may be chosen from the polyolefinically unsaturated compounds commonly used for crosslinking polymers obtained by radical polymerization. Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allyl or vinyl ethers of polyfunctional alcohols, and also the allylic esters of phosphoric and/or vinylphosphonic acid derivatives, or mixtures of these compounds.

According to a preferred embodiment of the invention, the crosslinking agent is chosen from methylenebisacrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The homopolymer includes only monomers bearing a sulfonic group and, if it is crosslinked, one or more crosslinking agents.

The preferred 2-acrylamido-2-methylpropanesulfonic acid homopolymers are generally characterized in that they comprise, randomly distributed:

a) from 90% to 99.9% by weight of units of general formula (1) below:

(1)

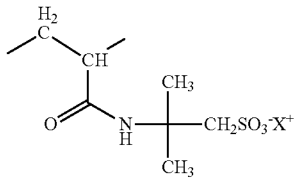

in which $X^+$ denotes a proton, an alkali metal cation, an alkaline-earth metal cation or the ammonium ion, not more than 10 mol % of the cations $X^+$ possibly being protons $H^+$;

b) from 0.01% to 10% by weight of crosslinking units originating from at least one monomer containing at least two olefinic double bonds; the weight proportions being defined relative to the total weight of the polymer.

The homopolymers according to the invention that are more particularly preferred comprise from 98% to 99.5% by weight of units of formula (1) and from 0.2% to 2% by weight of crosslinking units.

Polymers of this type that may notably be mentioned include the crosslinked and neutralized 2-acrylamido-2-methylpropanesulfonic acid homopolymer sold by the company Clariant under the trade name Hostacerin AMPS® (CTFA name: ammonium polyacryldimethyltauramide).

The polymer may also be an amphiphilic homopolymer (or hydrophobic modified homopolymer) chosen from random amphiphilic 2-acrylamido-2-methylpropanesulfonic acid polymers modified by reaction with a C6-C22 n-monoalkylamine or di-n-alkylamine, such as those described in WO-A-00/31154, which are grafted homopolymers.

A fourth family of suitable thickening polymers is represented by copolymers of acrylamido-2-methylpropanesulfonic acid or salts thereof and of one or more nonionic monomers. They may be crosslinked or non-crosslinked.

When the polymers are crosslinked, the crosslinking agents may be chosen from the polyolefinically unsaturated compounds commonly used for crosslinking polymers obtained by radical polymerization. Such agents are described above.

According to a preferred embodiment of the invention, the crosslinking agent is chosen from methylenebisacrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The copolymers according to the invention are obtained from AMPS® and from one or more hydrophilic or hydrophobic ethylenically unsaturated nonionic monomers and, if they are crosslinked, one or more crosslinking agents such as those defined above.

The 2-acrylamido-2-methylpropanesulfonic acid monomer of the copolymer contained in the composition in accordance with the invention is in free form or is partially or totally neutralized with a mineral base (sodium hydroxide, potassium hydroxide or aqueous ammonia) or an organic base, such as mono-, di- or triethanolamine, an aminomethylpropanediol, N-methylglucamine, basic amino acids, such as arginine and lysine, and also a mixture of these compounds.

Preferably, the 2-acrylamido-2-methylpropane sulfonic acid monomer is partially or totally salified in the form of the ammonium or sodium salt.

Preferably, the 2-acrylamido-2-methylpropane sulfonic acid monomer is totally salified, preferably in the form of the ammonium or sodium salt.

The AMPS® copolymers contain one or more nonionic monomers chosen from water-soluble ethylenically unsaturated monomers, hydrophobic monomers, or mixtures thereof.

Among the nonionic water-soluble monomers, examples that may be mentioned include:

- (meth)acrylamide,
- N-vinylacetamide and N-methyl-N-vinylacetamide,
- N-vinylformamide and N-methyl-N-vinylformamide,
- maleic anhydride,
- vinylamine,
- N-vinyllactams including a cyclic alkyl group containing from 4 to 9 carbon atoms, such as N-vinylpyrrolidone, N-butyrolactam and N-vinylcaprolactam,
- vinyl alcohol of formula $CH_2{=}CHOH$,
- the water-soluble vinyl monomers of formula (2) below:

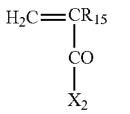

(2)

in which:

- $R_{15}$ is chosen from H, $—CH_3$, $—C_2H_5$ and $—C_3H_2$,
- $X_2$ is chosen from alkyl oxides of the type $—OR_{16}$ where $R_{16}$ is a linear or branched, saturated or unsaturated hydrocarbon-based radical containing from 1 to 6 carbon atoms, optionally substituted with a halogen atom (iodine, bromine, chlorine or fluorine); a hydroxyl (—OH) group; ether.

Mention is made, for example, of glycidyl (meth)acrylate, hydroxyethyl (meth)acrylate, and (meth)acrylates of ethylene glycol, of diethylene glycol or of polyalkylene glycol.

Preferably, the water-soluble monomer is chosen from acrylamide, vinylpyrrolidone and hydroxyalkyl (meth)acrylates, more particularly vinylpyrrolidone.

As copolymers of AMPS® in accordance with the invention with hydrophilic monomers, examples that may be mentioned include:

- copolymers of acrylamido-2-methylpropanesulfonic acid and of vinylpyrrolidone, notably such as the commercial product Aristoflex AVC sold by Clariant,
- crosslinked acrylamide/sodium acrylamido-2-methylpropanesulfonate copolymers, such as that used in the commercial product Sepigel 305® (INCI name: Polyacrylamide/$C_{13}$-$C_{14}$ isoparaffin/laureth-7) or that used in the commercial product sold under the name Simulgel 600® (INCI name: Acrylamide/sodium acryloyldimethyltaurate/isohexadecane/polysorbate-80®) by the company SEPPIC;
- copolymers of AMPS® and of hydroxyethyl acrylate, for instance the sodium AMPS®/hydroxyethyl acrylate copolymer, such as that used in the commercial product sold under the name Simulgel NS® by the company SEPPIC (INCI name: Hydroxyethyl acrylate/sodium acryloyldimethyltaurate copolymer (and) squalane (and) polysorbate 60);
- hydrophobically modified AMPS® copolymers such as the copolymer known under the INCI name: Ammonium acryloyldimethyltaurate/Steareth-25 methacrylate crosspolymer, sold under the trade name Aristoflex HMS by the company Clariant.

The concentration of anionic synthetic thickening polymer (i.e. of active material) generally ranges from 0.05% to 35% by weight relative to the total weight of the composition, preferably from 0.1% to 20% by weight, preferably from 0.2% to 10% by weight, preferably from 0.25% to 5% by weight and even more particularly from 0.3% to 3% by weight.

Thickening Polysaccharides

The composition according to the invention may also comprise a thickening polymer chosen from nonionic thickening polysaccharides, sulfate-based thickening polysaccharides and carboxylic branched thickening polysaccharides.

Among the nonionic thickening polysaccharides, mention may notably be made of nonionic cellulose-based thickening polysaccharides.

Preferably, the celluloses that may be used in the compositions according to the present invention are chosen from celluloses not including a hydrophobic chain and nonionic celluloses including one or more hydrophobic chains.

Preferably, the celluloses used according to the invention are cellulose ethers. Even more preferentially, these celluloses are nonionic hydroxyalkylcelluloses and in particular hydroxyethylcelluloses or hydroxypropylcelluloses. They may or may not contain a fatty chain. Among the nonionic celluloses not including a fatty chain, mention may be made of hydroxyethylcelluloses, hydroxypropylcelluloses, and hydroxypropylmethylcelluloses. A hydroxyethylcellulose that is particularly suitable for use is Cellosize HEC QP-4400 H sold by Amerchol (INCI name: Hydroxyethylcellulose).

The celluloses modified with groups including one or more nonionic fatty chains that can be used according to the present invention are notably:

- nonionic hydroxyethylcelluloses modified with groups including at least one fatty chain such as alkyl, arylalkyl or alkylaryl groups, or mixtures thereof, and in which the alkyl groups are preferably C8-C22 groups, such as the product Natrosol Plus Grade 330 CS® (C16 alkyls) sold by the company Ashland, corresponding to the INCI name Cetylhydroxyethylcellulose, or the product Bermocoll EHM 100® sold by the company AkzoNobel, those modified with alkylphenyl polyalkylene glycol ether groups, such as the product Amercell Polymer HM-1500® (nonylphenyl polyethylene glycol (15) ether) sold by the company Amerchol, corresponding to the INCI name Nonoxynyl hydroxyethylcellulose.

Among the sulfate-based thickening polysaccharides, mention may notably be made of rhamnose-free sulfate-based polysaccharides. These sulfate-based polysaccharides are preferably carrageenans.

Carrageenans are polysaccharides constituting the cell walls of various red algae (Rhodophyceae) belonging to the Gigartinacae, Hypneaceae, Furcellariaceae and Polyideaceae families. They include long galactan chains, anionic polyelectrolytes. Their molecular mass may be greater than 106. These linear polymers, formed with disaccharide units, are composed of two D-galactopyranose units linked alternately with α- and β-bonds. They are highly sulfated polysaccharides (20-50%) and the α-D-galactopyranosyl residues may be in 3',6'-anhydro form.

Initially, carrageenans were subdivided into two families according to their solubility in potassium chloride (KCl). The fractions soluble in KCl were designated by the prefix "kappa", whereas the term "lambda" was reserved for the insoluble fractions. Later, the classifications were based on the number and position of the sulfate groups and also on the presence of a 3',6'-anhydro bridge on the β-D-galactopyranosyl residues. This resulted in the four major families: κ, λ, β and ω.

The various types of carrageenans do not exist in pure form, but in the form of hybrids. Thus, in the natural state, κ- and i-carrageenans are in a kappa-iota hybrid form, but one of the two structures may dominate over the other. The κ-i hybrid state of a structure may be elucidated by using specific enzymes, which make it possible to enrich or reduce the content of one of the two forms. Carrageenans may coexist with their precursors. Carrageenans of different original families may coexist in a hybrid structure.

Preferably, the composition according to the invention comprises one or more sulfate-based polysaccharides of lambda carrageenan type. The sulfate-based polysaccharide of lambda carrageenan type may or may not be chemically modified. Preferably, the sulfate-based polysaccharide of lambda carrageenan type is not chemically modified. Preferably, the molecular weight (MW) of the polysaccharide is between 100 000 and 1 000 000 and more preferentially between 250 000 and 800 000. As sulfate-based polysaccharide of lambda carrageenan type, mention may be made of Satiagum UTC 10 or Satiagum VPC 410 from the company Cargill and Welgeenan ED 1039 from the company Eurogum.

Among the carboxylic branched thickening polysaccharides, mention may notably be made of anionic branched polysaccharides based on glucose, mannose, acetylated mannose, pyruvic acid and glucuronic acid. Such a polysaccharide is preferably xanthan.

Xanthan is a heteropolysaccharide produced on an industrial scale by the aerobic fermentation of the bacterium *Xanthomonas campestris*. Its structure consists of a main chain of β(1,4)-linked β-D-glucoses, similar to cellulose. One glucose molecule in two bears a trisaccharide side chain composed of an α-D-mannose, a β-D-glucuronic acid and a terminal β-D-mannose. The internal mannose residue is generally acetylated on carbon 6. About 30% of the terminal mannose residues bear a pyruvate group linked in chelated form between carbons 4 and 6. The charged pyruvic acids and glucuronic acids are ionizable, and are thus responsible for the anionic nature of xanthan (negative charge down to a pH equal to 1). The content of the pyruvate and acetate residues varies according to the bacterial strain, the fermentation process, the conditions after fermentation and the purification steps. These groups may be neutralized in commercial products with Na+, K+ or Ca2+ ions (Satia company, 1986). The neutralized form may be converted into the acid form by ion exchange or by dialysis of an acidic solution.

Xanthan gums have a molecular weight of between 1 000 000 and 50 000 000 and a viscosity of between 0.6 and 1.65 Pa·s for an aqueous composition containing 1% of xanthan gum (measured at 25° C. on a Brookfield viscometer of LVT type at 60 rpm).

Xanthan gums are represented, for example, by the products sold under the name Rhodicare® by the company PMC Ouvrie, under the name Satiaxane™ by the company Cargill Texturizing Solutions (for the food, cosmetic and pharmaceutical industries), under the name Novaxan™ by the company ADM, and under the names Kelzan® and Keltrol® by the company CP-Kelco.

The concentration of thickening polysaccharides used in the compositions according to the present invention ranges from 0.01% to 20%, preferably from 0.02% to 10%, preferably from 0.03% to 8%, preferably from 0.05% to 5% and even more preferably from 0.1% to 3% by weight relative to the total weight of the composition.

According to a preferred embodiment, the composition according to the invention comprises a thickener chosen from crosslinked acrylic acid homopolymers, crosslinked copolymers of (meth)acrylic acid and of a C1-C6 alkyl acrylate, copolymers of acrylamido-2-methylpropanesulfonic acid with one or more nonionic monomers, crosslinked and preferably neutralized 2-acrylamido-2-methylpropanesulfonic acid homopolymers, hydroxyethylcelluloses, carrageenans and xanthan gum.

According to a preferred embodiment, the composition according to the invention comprises a thickener chosen from crosslinked acrylic acid homopolymers, crosslinked and preferably neutralized 2-acrylamido-2-methylpropanesulfonic acid homopolymers, hydroxyethylcelluloses, carrageenans and xanthan gum.

The composition according to the invention may also comprise a mixture of several thickening polymers, typically of at least two or more thickening polymers. The composition may typically comprise at least one anionic synthetic thickening polymer and at least one thickener chosen from nonionic thickening polysaccharides, sulfate-based thickening polysaccharides, carboxylic branched thickening polysaccharides, and mixtures thereof.

According to a particular embodiment of the invention, the total concentration of thickener(s) used in the composition ranges from 0.01% to 50%, preferably from 0.1% to 20%, preferably from 0.2% to 10%, preferably from 0.3% to 8% and even more preferably from 0.5% to 3% by weight relative to the total weight of the composition.

Surfactants with an HLB of Greater than or Equal to 7

The composition according to the invention comprises at least one surfactant with an HLB of greater than or equal to 7.

The term "HLB" (hydrophilic-lipophilic balance) is well known to those skilled in the art, and denotes the hydrophilic-lipophilic balance of a surfactant at 25° C. in the Griffin sense.

The term "hydrophilic-lipophilic balance (HLB)" means the equilibrium between the size and strength of the hydrophilic group and the size and strength of the lipophilic group of the surfactant. The HLB value according to Griffin is defined in J. Soc. Cosm. Chem. 1954 (volume 5), pages 249-256.

The surfactant(s) with an HLB of greater than or equal to 7 may be ionic or nonionic. Use may notably be made of the surfactants with an HLB of greater than or equal to 7 which are mentioned in the reference handbook McCutcheons Emulsifiers & Detergents, International Edition from 1998 et seq.

Reference may also be made to *Kirk-Othmer's Encyclopedia of Chemical Technology*, volume 22, pages 333-432, 3rd edition, 1979, Wiley, for the definition of the emulsifying properties and functions of surfactants, in particular pages 347-377 of this reference, for nonionic surfactants.

For the ionic surfactants, the HLB values of surfactants in the form of individual molecules may be calculated by applying Davies' formula. According to this formula, the HLB is derived by adding the hydrophilic/hydrophobic contributions provided by the structural components of the surfactant:

$$HLB=\Sigma(\text{contributions of the hydrophilic groups})-\Sigma(\text{contributions of the hydrophobic groups})+7. \quad \text{[Math. 1]}$$

Griffin's formula is generally used for nonionic surfactants and Davies' formula is used for ionic surfactants.

The HLB values are defined at room temperature.

Advantageously, the composition according to the invention comprises at least one surfactant with an HLB of greater than 7 and preferably less than 40, preferably greater than 10 and less than 20, for example between 10 and 20.

According to one embodiment, the composition according to the invention comprises one or more surfactants with an HLB of greater than or equal to 7, chosen from nonionic, amphoteric and anionic surfactants.

The nonionic surfactants may be chosen, for example, from:

- esters of fatty acids, notably of $C_8$-$C_{24}$ fatty acids, and of sugars and ethers of fatty alcohols, notably of $C_8$-$C_{24}$ fatty alcohols, and of sugars;
- oxyalkylenated glycerol ethers, in particular oxyethylenated and/or oxypropylenated glycerol ethers, which may include from 5 to 100 oxyethylene and/or oxypropylene units, preferably 10 to 80 oxyethylene and/or oxypropylene units;
- oxyalkylenated alcohols, in particular oxyethylenated and/or oxypropylenated alcohols, which may include from 5 to 100 oxyethylene and/or oxypropylene units, preferably from 10 to 100 oxyethylene units, in particular ethoxylated, notably $C_8$-$C_{24}$ and preferably $C_{12}$-$C_{18}$ fatty alcohols such as stearyl alcohol ethoxylated with 20 oxyethylene units (CTFA name: Steareth-20) such as Brij 78 sold by the company Croda, cetyl alcohol ethoxylated with 20 oxyethylene groups (CTFA name: Ceteth-20), cetearyl alcohol ethoxylated with 30 oxyethylene units (CTFA name: Ceteareth-30), and the mixture of $C_{12}$-$C_{15}$ fatty alcohols including 7 oxyethylene units (CTFA name: $C_{12-15}$ Pareth-7), for instance the product sold under the name Neodol 25-7® by Shell Chemicals;
- esters of a fatty acid, notably of a $C_8$-$C_{24}$ and preferably $C_{16}$-$C_{22}$ fatty acid, and of polyethylene glycol (or PEG) (which may comprise from 5 to 100 oxyethylene units, preferably from 10 to 80 oxyethylene units), such as PEG-50 stearate and PEG-40 monostearate sold under the name Myrj 52P® by the company Uniqema, or PEG-75 stearate;
- esters of a fatty acid, notably a $C_8$-$C_{24}$ and preferably $C_{16}$-$C_{22}$ fatty acid, and of oxyalkylenated glycerol ethers, in particular oxyethylenated and/or oxypropylenated glycerol ethers (which may include from 5 to 100 oxyethylene and/or oxypropylene units), for instance polyoxyethylenated glyceryl monostearate containing 200 oxyethylene units, sold under the name Simulsol 220 TM® by the company SEPPIC; polyoxyethylenated glyceryl stearate containing 30 oxyethylene units, for instance the product Tagat S® sold by the company Evonik Goldschmidt, polyoxyethylenated glyceryl oleate containing 30 oxyethylene units, for instance the product Tagat O® sold by the company Evonik Goldschmidt, polyoxyethylenated glyceryl cocoate containing 30 oxyethylene units, for instance the product Varionic LI 13® sold by the company Sherex, polyoxyethylenated glyceryl isostearate containing 30 oxyethylene units, for instance the product Tagat L® sold by the company Evonik Goldschmidt, and polyoxyethylenated glyceryl laurate containing 30 oxyethylene units, for instance the product Tagat I® from the company Evonik Goldschmidt;
- esters of a fatty acid, notably a $C_8$-$C_{24}$ and preferably $C_{16}$-$C_{22}$ fatty acid, and of sorbitol, which are advantageously oxyalkylenated, in particular oxyethylenated and/or oxypropylenated (which may include from 5 to 100 oxyethylene and/or oxypropylene units), for instance sorbitan monostearate oxyethylenated with 20 mol of ethylene oxide (INCI name=Polysorbate-60) notably sold under the name Tween 60® by the company Croda, and more particularly sorbitan monolaurate oxyethylenated with 20 mol of ethylene oxide (INCI name=Polysorbate-20) notably sold under the name Tween 20® by the company Croda and sorbitan monooleate oxyethylenated with 20 mol of ethylene oxide (INCI name=Polysorbate-80) notably sold under the name Tween 80® by the company Croda;
- silicone surfactants;
- copolymers of propylene oxide and of ethylene oxide, also known as EO/PO polycondensates;
- and mixtures thereof.

The fatty acid esters of sugars that may be used as nonionic surfactant above may preferably be solid at a temperature of less than or equal to 45° C. and may be chosen in particular from the group comprising esters or mixtures of esters of $C_8$-$C_{22}$ fatty acid and of sucrose, maltose, glucose or fructose, and esters or mixtures of esters of $C_{14}$-$C_{22}$ fatty acid and of methylglucose.

As examples of esters or mixtures of esters of fatty acid and of sucrose, maltose, glucose or fructose, mention may be made of sucrose monostearate, sucrose distearate and sucrose tristearate and mixtures thereof, such as the products sold by the company Croda under the name Crodesta F50, F70, F110 and F160; and an example of esters or mixtures of esters of fatty acid and of methylglucose that may be mentioned is methylglucose-polyglyceryl-3 distearate, sold by the company Evonik Goldschmidt under the name Tego-Care 450. Mention may also be made of glucose or maltose monoesters such as methyl-o-hexadecanoyl-6-D-glucoside and o-hexadecanoyl-6-D-maltoside.

The ethers of a fatty alcohol, notably a $C_8$-$C_{24}$ fatty alcohol, and of sugars, that may be used as nonionic surfactant above may be solid at a temperature of less than or equal to 45° C. and may be chosen in particular from the group comprising ethers or mixtures of ethers of a $C_8$-$C_{22}$ fatty alcohol and of glucose, maltose, sucrose or fructose, and ethers or mixtures of ethers of a $C_{14}$-$C_{22}$ fatty alcohol and of methylglucose. These are in particular alkylpolyglucosides.

The $C_8$-$C_{22}$ or $C_{14}$-$C_{22}$ fatty alcohols forming the fatty unit of these ethers may comprise a saturated or unsaturated linear alkyl chain containing, respectively, from 8 to 22 or from 14 to 22 carbon atoms. The fatty unit of the ethers may be chosen in particular from decyl, cetyl, behenyl, arachidyl, stearyl, palmityl, myristyl, lauryl, capryl and hexadecanoyl units, and mixtures thereof such as cetearyl.

As examples of fatty alcohol ethers of sugars, mention may be made of (C8-C22)alkylpolyglucosides such as decyl glucoside and lauryl glucoside, sold, for example, by the company BASF under the respective names Plantaren 2000 and Plantaren 1200, cetostearyl glucoside optionally as a mixture with cetostearyl alcohol, sold, for example, under the name Montanov 68 by the company SEPPIC, under the name Tego-Care CG90 by the company Evonik Goldschmidt and under the name Emulgade KE3302 by the company BASF, and also arachidyl glucoside, for example in the form of a mixture of arachidyl alcohol and behenyl alcohol and arachidyl glucoside, sold under the name Montanov 202 by the company SEPPIC.

The surfactant used is more particularly sucrose monostearate, sucrose distearate or sucrose tristearate and mixtures thereof, methyl glucose-polyglyceryl-3 distearate and (C8-C22)alkylpolyglucosides.

The fatty acid esters of glycerol that may be used as nonionic surfactant above, which are solid at a temperature of less than or equal to 45° C., may be chosen in particular from the group comprising esters formed from at least one acid comprising a saturated linear alkyl chain containing from 12 to 22 carbon atoms and from 1 to 12 glycerol units. One or more of these fatty acid esters of glycerol may be used in the present invention.

These esters may be chosen in particular from glyceryl stearates, behenates, arachidates and palmitates, and mixtures thereof. Glyceryl stearates and palmitates are preferably used.

As examples of surfactants that may be used in the present invention, mention may be made of decaglyceryl monostearate, distearate, tristearate and pentastearate (CTFA names: polyglyceryl-10 stearate, polyglyceryl-10 distearate, polyglyceryl-10 tristearate, polyglyceryl-10 pentastearate), such as the products sold under the respective names Nikkol Decaglyn 1 S, 2 S, 3 S and 5 S by the company Nippon Surfactant Industries, and diglyceryl monostearate (CTFA name: polyglyceryl-2 stearate), such as the product sold by the company Nikko under the name Nikkol DGMS.

The fatty acid esters of sorbitan that may be used as nonionic surfactant above may be chosen from the group comprising esters of a $C_{16}$-$C_{22}$ fatty acid and of sorbitan and oxyethylenated esters of a $C_{16}$-$C_{22}$ fatty acid and of sorbitan. They are formed from at least one fatty acid comprising at least one saturated linear alkyl chain containing, respectively, from 16 to 22 carbon atoms and from sorbitol or ethoxylated sorbitol. The oxyethylenated esters generally comprise from 2 to 100 ethylene glycol units and preferably from 4 to 40 ethylene oxide (EO) units.

These esters may be chosen in particular from stearates, behenates, arachidates and palmitates, and mixtures thereof. Stearates and palmitates are preferably used.

As examples of the above nonionic surfactant that may be used in the present invention, mention may be made of sorbitan monostearate (CTFA name: sorbitan stearate), sold by the company Croda under the name Span 60, sorbitan monopalmitate (CTFA name: sorbitan palmitate), sold by the company Croda under the name Span 40, and sorbitan tristearate 20 EO (CTFA name: polysorbate 65), sold by the company Croda under the name Tween 65.

EO/PO polycondensates are more particularly copolymers formed from polyethylene glycol and polypropylene glycol blocks, for instance polyethylene glycol/polypropylene glycol/polyethylene glycol triblock polycondensates. These triblock polycondensates have, for example, the following chemical structure:

$$H—(O—CH_2—CH_2)_a—(O—CH(CH_3)—CH_2)_b—(O—CH_2—CH_2)_c—OH,$$

in which formula a ranges from 2 to 120 and b ranges from 1 to 100.

The EO/PO polycondensates preferably have a weight-average molecular mass ranging from 1000 to 15 000 and better still ranging from 2000 to 13 000. Advantageously, said EO/PO polycondensates have a cloud point, at 10 g/l in distilled water, of greater than or equal to 20° C., preferably of greater than or equal to 60° C. The cloud point is measured according to the standard ISO 1065. As EO/PO polycondensates that may be used according to the invention, mention may be made of the polyethylene glycol/polypropylene glycol/polyethylene glycol triblock polycondensates sold under the name Synperonic®, such as Synperonic PE/L44® and Synperonic PE/F127® by the company Croda.

The amphoteric surfactants may be chosen, for example, from betaines, N-alkylamido betaines and derivatives thereof, glycine derivatives, sultaines, alkyl polyaminocarboxylates, alkylamphoacetates, and mixtures thereof.

Examples of betaines that may be mentioned include cocoyl betaine, such as the product sold under the name Dehyton AB-30® by the company BASF or sold under the name Empigen BB® by the company Innospec Active Chemicals, lauryl betaine, such as the product sold under the name Genagen KB® by the company Clariant, oxyethylenated (10 EO) lauryl betaine, such as the product sold under the name Lauryl Ether (10 EO) Betaine® by the company Shin Nihon Rica, or oxyethylenated (10 EO) stearyl betaine, such as the product sold under the name Stearyl Ether (10 EO) Betaine® by the company Shin Nihon Rica.

Among the N-alkylamido betaines and derivatives thereof, examples that may be mentioned include the cocamidopropyl betaine sold under the name Lebon 2000 HG® by the company Sanyo or the lauramidopropyl betaine sold under the name Rewoteric AMB12P® by the company Evonik Goldschmidt.

A glycine derivatives that may be mentioned is sodium N-cocoylglycinate sold under the name Amilite GCS-12® by the company Ajinomoto.

A sultaine that may be mentioned is cocoylamidopropyl hydroxysulfobetaine, sold under the name Crosultaine C-50® by the company Croda.

Alkyl polyaminocarboxylates (APACs) that may be mentioned include sodium cocoylpolyaminocarboxylate, sold under the names Ampholak 7 CX/C® and Ampholak 7 CX® by the company AkzoNobel, sodium stearylpolyamidocarboxylate, sold under the name Ampholak 7 TX/C by the company AkzoNobel, or sodium carboxymethyloleylpolypropylamine, sold under the name Ampholak XO7/C® by the company AkzoNobel.

Alkylamphoacetates that may be mentioned include the compounds corresponding to the general formula (II) below:

(II)

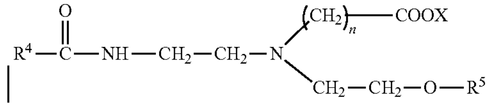

in which:

R4 represents a saturated or unsaturated hydrocarbon-based radical, such as a fatty acid residue, R5 represents a hydrogen atom or the group —(CH2)m-COOY, X and Y represent, independently or simultaneously, a hydrogen atom or a monovalent, notably metallic cation and in particular a cation of an alkali metal such as sodium, n and m are two integers which may be, independently or simultaneously, equal to 1 or 2.

The amphoteric surfactants of formula (II) above that particularly fall within the scope of the present invention are those having at least one, and preferably several, of the following characteristics: n and m are identical; R5 represents the group —(CH2)m-COOY; X and Y are identical and preferably represent a monovalent metal cation, particularly sodium; R4 represents an alkyl radical generally of C5-C20, notably C7, C9, C11, C13 or C17, an unsaturated C17 radical, or an alkyl radical of an acid R4-COOH present in natural oils, such as coconut, coconut kernel, linseed or wheat germ oil or animal tallow.

As concrete examples of amphoteric surfactants of imidazoline type, mention may notably be made of those sold under the general trade name Miranol® by the company Rhodia Chimie, and also those having the following CTFA names (CTFA dictionary, fourth edition, 1991) which follow:

Disodium Caproamphodiacetate,
Disodium Caproamphodipropionate,
Disodium Capryloamphodiacetate,
Disodium Capryloamphodipropionate,
Disodium Cocoamphodiacetate,
Disodium Cocoamphodipropionate,
Disodium Isostearoamphodiacetate,
Disodium Isostearoamphodipropionate,
Disodium Lauroamphodiacetate,
Disodium Lauroamphodipropionate,
Disodium Oleoamphodipropionate,
Disodium Stearoamphodiacetate,
Disodium Tallowamphodiacetate, and
Disodium Wheatgermamphodiacetate.

The anionic surfactants are preferably chosen from:

gemini surfactants, for instance the disodium ethylene dicocamide PEG-15 disulfate (INCI name) sold, for example, under the trade name Ceralution H;

the salts, in particular alkali metal salts, notably sodium salts, ammonium salts, amine salts such as amino alcohol salts, or alkaline-earth metal salts such as magnesium salts, of the following compounds:

alkyl sulfates, alkyl ether sulfates, alkylamido ether sulfates, alkylaryl polyether sulfates, monoglyceride sulfates;

alkyl sulfonates, alkyl amide sulfonates, alkyl aryl sulfonates, α-olefin sulfonates, paraffin sulfonates;

alkyl phosphates, alkyl ether phosphates;

alkylsulfosuccinates, alkyl ether sulfosuccinates, alkylamidesulfosuccinates; alkylsulfosuccinates;

alkyl sulfoacetates;

acyl sarcosinates; acylisethionates and N-acyl taurates;

salts of fatty acids such as oleic acid, ricinoleic acid, palmitic acid or stearic acid, coconut kernel oil acid or hydrogenated coconut kernel oil acid;

alkyl-D-galactoside uronic acid salts;

acyl lactylates;

salts of polyoxyalkylenated alkyl ether carboxylic acids, of polyoxyalkylenated alkylaryl ether carboxylic acids or of polyoxyalkylenated alkylamido ether carboxylic acids, in particular those including from 2 to 50 ethylene oxide groups;

and mixtures thereof.

The alkyl or acyl radical of these various compounds advantageously includes from 6 to 24 carbon atoms, and preferably from 8 to 24 carbon atoms, and the aryl radical preferably denotes a phenyl or benzyl group.

Preferably a (C12-C20)alkyl phosphate and particularly a cetyl phosphate will be used, for example potassium cetyl phosphate, such as the product sold, for example, under the trade name Amphisol K:

glyceryl stearate (and) disodium ethylene dicocamide PEG-15 disulfate (and) glyceryl stearate citrate, a $C_{12}$-$C_{20}$ fatty acid salt such as triethanolamine stearate-glyceryl stearate (and) PEG-100 Stearate (INCI name), alone or as a mixture, sold, for example, under the trade name Arlacel 165, stearic acid, stearyl alcohol, and any mixture thereof.

According to the invention, the surfactant with an HLB of greater than or equal to 7 is preferably a nonionic surfactant.

According to a particular embodiment, the surfactants in accordance with the invention are chosen from water-soluble silicones including at least one terminal or pendent monovalent polyoxyalkylene group.

The surfactants in accordance with the invention are preferably chosen from water-soluble silicones including at least one polyoxyalkylene group of general formula (a) below:

$$R_3SiO(R_2SiO)_p(RPESiO)_qSiR_3 \quad (a)$$

in which:

the radicals R, which may be identical or different, denote a monovalent hydrocarbon-based radical chosen from alkyl, aryl and aralkyl radicals containing not more than 10 carbon atoms; some of the radicals R may also additionally contain an ethylcyclohexylene monoxide group of formula:

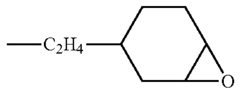

and are in small proportion in the polysiloxane chain;

p ranges from 0 to 150, preferably from 0 to 100 and more preferentially from 0 to 30;

q ranges from 1 to 12, preferably from 1 to 10 and more preferentially from 1 to 8; and the polyether group PE has the formula (b) below:

$$—C_xH_{2x}(OC_2H_4)_y(OC_3H_6)_zOR' \quad (b)$$

in which:

x ranges from 1 to 8, preferably from 2 to 4 and is more preferentially equal to 3;

y is greater than 0;

z is greater than or equal to 0;

the values of y and z being such that the total molecular weight of the polyoxyalkylene portion of the polyether group PE ranges from 200 to 10 000 and more preferentially from 350 to 4000; and R' denotes hydrogen, a $C_1$ to $C_8$ alkyl group or a $C_2$ to $C_8$ acyl group.

It should be noted that when z is other than 0, the polyoxyethylene and polyoxypropylene units may be randomly distributed along the polyether chain PE or distributed in blocks or else distributed both in blocks and randomly.

Preferably, the radicals R are chosen from $C_1$-$C_6$ lower alkyl radicals such as methyl, ethyl, butyl, hexyl; phenyl and benzyl. More particularly, the radicals R are chosen from $C_1$-$C_4$ lower alkyl radicals, and even more particularly denote methyl.

Preferably, the radicals R' are chosen from $C_1$-$C_4$ lower alkyls and even more particularly denote methyl.

The number of oxyethylene units in the group PE must be sufficient to produce a turbidity point in water of between 25 and 90° C. and more preferentially from 40 to 70° C.

Water-soluble silicones of formula (a) may be obtained according to the process described in patent U.S. Pat. No. 4,847,398.

Among the water-soluble silicones of formula (a), use will preferably be made of the silicone of formula (a') below:

$$MeSiO(MeSiO)_p(MePESiO)_qSiMe_3 \quad (a')$$

in which Me denotes methyl and PE denotes:

$$—(CH_2)_3O(OC_2H_4)_y(OC_3H)_zOR' \quad (b')$$

in which y and z have the same values indicated above and R' denotes hydrogen or a $C_1$-$C_4$ alkyl group and more particularly methyl.

As another family of water-soluble silicones that may be used according to the invention, mention may be made of the branched silicones of formula (c) below:

$$(MeSiO)_{q-2}[(SiOMe_2)_{p/q}OPE]_q \quad (c)$$

in which p and q have the same values indicated above in formula (a); Me means methyl; and PE denotes the group of formula (d) below:

$$—(OC_2H_4)_y(OC_3H)_zR' \quad (d)$$

in which y and z have the same values indicated above in formula (b) and R' denotes a $C_1$-$C_4$ alkyl group and more particularly methyl.

Such silicones are sold, for example, by the company Momentive Performance Materials under the trade names Silwet L-720®, Silwet L-7002®, Silwet L-7600®, Silwet L-7604®, Silwet L-7605®, Silwet L-7607®, Silwet 1614®, Silwet L-7657®, Silwet L-7200®, Silwet L7230®, Silsoft 305®, Silsoft 820®, Silsoft 880® or by the company Evonik Goldschmidt under the trade names Tego wet 260®, Tegowet 500®, Tegowet 505® and Tegowet 510®.

The silicone surfactants are notably:

- bis-PEG/PPG-16/16 PEG/PPG-16/16 dimethicone (INCI name), sold, for example, under the trade name Abil Care 85 by Evonik Goldschmidt,
- PEG-12 dimethicone (INCI name), sold, for example, under the trade name Silsoft 880 by the company Momentive Performance Materials,
- bis-PEG-18 methyl ether dimethyl silane,
- PEG-11 methyl ether dimethicone, sold, for example, under the trade name KF 351 by the company Shin-Etsu, and
- dimethicone copolyol benzoate (partial ester of benzoic acid and of dimethicone copolyol, the latter being a dimethylpolysiloxane polymer including polyoxyethylene and/or polyoxypropylene side chains), sold, for example, under the name Finsolv SLB 101® and 201® by the company Innospec Active Chemicals.

According to a particular embodiment of the invention, the surfactant(s) with an HLB of greater than or equal to 7 are chosen from:

- esters of a fatty acid, notably of a $C_8$-$C_{24}$ and preferably $C_{16}$-$C_{22}$ fatty acid, and of sorbitol, which are advantageously oxyalkylenated, in particular oxyethylenated and/or oxypropylenated (which may include from 5 to 100 oxyethylene and/or oxypropylene units), such as Polysorbate-20 and Polysorbate 80;
- water-soluble silicones including at least one terminal or pendent monovalent polyoxyalkylene group, such as PEG-12 dimethicone, PEG-11 methyl ether dimethicone;
- and mixtures thereof.

According to a particular embodiment of the invention, the surfactant(s) with an HLB of greater than or equal to 7 are present in concentrations ranging from 0.1% to 5% by weight, preferably from 0.5% to 5%, more particularly from 0.5% to 3% by weight and better still from 0.7% to 2% by weight, relative to the total weight of the composition.

Aqueous Phase

The composition according to the invention comprises a physiologically acceptable aqueous medium.

Preferably, the composition according to the invention comprises an aqueous medium comprising at least water.

The aqueous medium may comprise at least one other organic solvent that is soluble in water, at 25° C., chosen, for example, from:

- C1-C4 monoalkanols. The term "$C_1$-$C_4$ monoalkanol" means any linear or branched saturated alkane compound containing from 1 to 4 carbon atoms and only one hydroxyl (OH) function. The $C_1$-$C_4$ monoalkanol(s) present in the compositions of the invention may be chosen from methanol, ethanol, propanol, isopropanol and butanol, or mixtures thereof. Ethanol will be chosen more particularly;
- polyols notably containing from 2 to 20 carbon atoms, preferably from 2 to 6 carbon atoms, for instance glycerol, diglycerol, propylene glycol, isoprene glycol, dipropylene glycol, butylene glycol, hexylene glycol, 1,3-propanediol, pentylene glycol, simple sugars, water-soluble polyalkylene glycols; and
- mixtures thereof.

Preferably, the composition according to the invention comprises at least one C1-C4 monoalkanol, and more particularly ethanol.

The monoalkanols are generally present in concentrations ranging from 0.2% to 90% by weight, more preferentially from 0.5% to 50% and preferably from 1% to 10% by weight relative to the total weight of the composition.

According to a particular embodiment, the composition according to the invention comprises at least one polyol, notably as described above. The presence of at least one polyol makes it possible notably to improve the cosmetic properties, such as the glidance on application, and reduces the tackiness. Preferably, it comprises at least 1% by weight of polyol(s) relative to the total weight of the composition, preferably at least 5% by weight of polyol(s) relative to the total weight of the composition, preferably from 8% to 50% by weight, preferably from 10% to 40% by weight, preferably from 15% to 35% by weight, better still from 18% to 30% by weight and even more preferentially from 20% to 30% by weight.

Preferably, the composition according to the invention comprises a polyol, preferably glycerol, butylene glycol, propylene glycol or dipropylene glycol, and mixtures thereof.

The composition preferably comprises from 20% to 99% by weight of water relative to the total weight of the composition, preferably from 30% to 90% by weight, preferably from 35% to 80%, preferably from 40% to 70% by weight.

According to one embodiment, the cosmetic composition according to the invention may comprise an acid and/or a base.

Preferably, the composition according to the invention has a pH of between 4 and 10, preferably between 6 and 9 and preferentially between 6.5 and 8.

Viscosity

The compositions according to the invention advantageously have a viscosity of at least 0.10 poises (Pa·s), measured at 25° C. with a Rheomat RM100® viscometer from Lamy Rheology. Preferably, it is between 0.20 poises and 230 poises, preferably between 0.20 and 15 poises, preferably between 0.90 and 15 poises (Pa·s).

According to a particular embodiment, the composition according to the invention also comprises cosmetically acceptable active agents and/or excipients.

The term "cosmetically acceptable" means compatible with the skin and/or its integuments, having a pleasant colour, odour and feel and not causing any unacceptable discomfort (stinging, tautness or redness) liable to discourage the consumer from using this composition.

The compositions according to the invention may be in the form of an aqueous solution or an aqueous gel. According to a preferred embodiment, the composition is in the form of an aqueous gel.

The composition of the invention does not comprise any fatty or oily phase. Preferably, the compositions according to the invention are oil-free. For the purposes of the invention, the term "oil-free" denotes a composition comprising only one liquid phase, which is an aqueous phase (a liquid phase comprising water). The term "oil" does not cover, for example, water-soluble active ingredients, water-soluble UV-screening agents and water-soluble glycols.

Finally, a subject of the present invention is also a non-therapeutic cosmetic process for treating keratin materials, preferably the skin, comprising the application to said keratin materials of a composition according to the invention. Such a process is notably directed towards protecting the keratin materials, and notably the skin, against UV radiation.

Concrete but in no way limiting examples illustrating the invention will now be given.

In the examples, the temperature is room temperature (20° C.) and is expressed in degrees Celsius, unless otherwise indicated, and the pressure is atmospheric pressure, unless otherwise indicated.

The examples that follow will allow the invention to be understood more clearly, without, however, being limiting in nature. The amounts indicated are weight percentages of starting material, unless otherwise mentioned. The names of the compounds are given as the chemical names or the INCI names.

EXAMPLES

Compositions A to F of Examples 1 and 2 below were prepared as follows.

The compositions according to the invention are compositions B and E.

The comparative compositions are indicated by an asterisk; they are the compositions A, C, D and F. Specifically, comparative compositions A and D differ from the compositions according to the invention in that they do not contain any surfactant with an HLB of greater than or equal to 7. Compositions C and F differ from the compositions of the invention in that they do not contain any thickener.

In the tables below, the term "a.m." means "active material".

Procedure:

1) Mix the components of the gelled phase while taking care to neutralize the carbomer.
2) In a separate beaker, prepare the mixture of the screening phase.
3) Add the screening phase to the gelled phase.
4) Add the alcohol, and then the surfactant.

in vivo: Evaluation of the Sun Protection Factor (SPF) of the formulations was performed in vivo on five individuals according to the protocol ISO/EN 24444 "Cosmetics—Sun protection test methods—in-vivo determination of the sun protection factor (SPF) (2010)".

Example 1: Preparation and Evaluation of Compositions According to the Invention and of Comparative Compositions The following compositions were prepared.

TABLE 1

| Phases | Compositions | A* (comparative) | B (invention) | C* (comparative) |
|---|---|---|---|---|
| Gelled phase | Water | qs 100 | qs 100 | qs 100 |
| | Preserving agents | qs | qs | qs |
| | Carbomer (Carbopol 980) | 0.5 | 0.5 | — |
| | Tromethamine | 0.9 | 0.9 | — |
| | Xanthan gum (Keltrol CG-T CP Kelco) | 0.3 | 0.3 | — |
| | Carrageenan (Satiagum VPC 410 Cargill) | 0.5 | 0.5 | — |
| | Glycerol | 2 | 2 | 2 |
| | Propylene glycol | 19 | 19 | 19 |
| | Butylene glycol | 6.4 | 6.4 | 6.4 |

TABLE 1-continued

| Phases | Compositions | A* (comparative) | B (invention) | C* (comparative) |
|---|---|---|---|---|
| Screening aqueous phase | Water | 15 | 15 | 15 |
| | Phenylbenzimidazolesulfonic acid, (Eusolex 232 from Merck) | 8 | 8 | 8 |
| | Terephthalylidenedicamphorsulfonic acid, (Mexoryl SX from Chimex; 33% a.m.) | 10 (3.3% a.m.) | 10 (3.3% a.m.) | 10 (3.3% a.m.) |
| | Triethanolamine | 2.5 | 2.5 | 2.5 |
| | Arginine | 5 | 5 | 5 |
| | Alcohol | 4 | 4 | 4 |
| | Oxyethylenated (20 EO) sorbitan monolaurate (Tween 20 ® from Croda) | — | 1 | 1 |
| in vivo SPF | | 18.6 ± 2.4 | 28.3 ± 2.8 | 13.7 ± 1.8 |

These results show the importance of the presence of a surfactant with an HLB of greater than or equal to 7 and of a hydrophilic thickener for obtaining improved SPF values.

Once prepared, the various compositions are tested as regards their appearance (homogeneity/compatibility), and their viscosity is measured.

The viscosity is measured as indicated in the description.

The results are given in Table 2.

TABLE 2

| Formulation | A* (comparative) | B (invention) | C* (comparative) |
|---|---|---|---|
| Homogeneity | Homogeneous | Homogeneous | Homogeneous |
| Viscosity (in poises) | 2.8 | 2.7 | <0.2 |

Example 2: Preparation and Evaluation of Compositions According to the Invention and of Comparative Compositions The following compositions were prepared.

TABLE 3

| Phases | Compositions | D* (comparative) | E (invention) | F* (comparative) |
|---|---|---|---|---|
| Gelled phase | Water | qs 100 | qs 100 | qs 100 |
| | Preserving agents | qs | qs | qs |
| | Carbomer (Carbopol 980) | 0.5 | 0.5 | — |
| | Tromethamine | 0.9 | 0.9 | — |
| | Xanthan gum (Keltrol CG-T CP Kelco) | 0.3 | 0.3 | — |
| | Carrageenan (Satiagum VPC 410 Cargill) | 0.5 | 0.5 | — |
| | Glycerol | 1 | 1 | 1 |
| | Propylene glycol | 7.9 | 7.9 | 7.9 |
| | Butylene glycol | 9.7 | 9.7 | 9.7 |
| Screening aqueous phase | Water | 15 | 15 | 15 |
| | Phenylbenzimidazolesulfonic acid, (Eusolex 232 from Merck) | 8 | 8 | 8 |
| | Terephthalylidenedicamphorsulfonic acid, (Mexoryl SX from Chimex; 33% a.m.) | 10 (3.3% a.m.) | 10 (3.3% a.m.) | 10 (3.3% a.m.) |
| | Triethanolamine | 2.5 | 2.5 | 2.5 |
| | Arginine | 5 | 5 | 5 |
| | Alcohol | 4 | 4 | 4 |
| | Oxyethylenated (20 EO) sorbitan monolaurate (Tween 20 ® from Croda) | — | 1 | 1 |
| in vivo SPF | | 32.8 ± 4.4 | 42.9 ± 4.9 | 23.7 ± 1.4 |

These results show the importance of the presence of a surfactant with an HLB of greater than or equal to 7 and of a hydrophilic thickener for obtaining improved SPF values.

Once prepared, the various compositions are tested as regards their appearance (homogeneity/compatibility), and their viscosity and turbidity are measured.

The viscosity and the turbidity are measured as indicated in the description.

The results are given in Table 4.

TABLE 4

| Formulation | D* (comparative) | E (invention) | F* (comparative) |
|---|---|---|---|
| Homogeneity | Homogeneous | Homogeneous | Homogeneous |
| Viscosity (in poises) | 5.5 | 5.7 | <0.2 |
| Turbidity (in NTU) | 85.30 | 93.80 | 1.02 |

The invention claimed is:

1. An aqueous cosmetic composition comprising between 0.2% and 40% by weight relative to the total weight of the composition of at least one screening agent chosen from water-soluble or water-dispersible screening agents that are capable of absorbing UV rays from 320 to 400 nm (UVA), water-soluble or water-dispersible screening agents that are capable of absorbing UV rays from 280 to 320 nm (UVB), and mixtures thereof; from 0.01% to 50% by weight, relative to the total weight of the composition of at least one hydrophilic thickener; and from 0.1% to 5% by weight relative to the total weight of the composition of at least one surfactant with an HLB of greater than or equal to 7, and wherein the composition contains less than 10% by weight of a fatty phase; and wherein the composition is totally free of gellan gum.

2. The composition according to claim 1 which is transparent or translucent.

3. The composition according to claim 1 having an amount of fatty phase of less than 5% by weight of the composition.

4. The composition according to claim 1, comprising at least one screening agent chosen from water-soluble screening agents that are capable of absorbing UV rays from 320 to 400 nm (UVA), water-soluble screening agents that are capable of absorbing UV rays from 280 to 320 nm (UVB), and mixtures thereof.

5. The composition according to claim 1, comprising at least one water-soluble screening agent that is capable of absorbing UV rays from 320 to 400 nm (UVA) and at least one water-soluble screening agent that is capable of absorbing UV rays from 280 to 320 nm (UVB).

6. The composition according to claim 1, in which the at least one screening agent is chosen from water-soluble organic screening agents.

7. The composition according to claim 1, in which the water-soluble screening agents that are capable of absorbing UV rays from 320 to 400 nm (UVA) are chosen from benzene-1,4-bis(3-methylidene-10-camphorsulfonic acid) (INCI name: Terephthalylidene Dicamphor Sulfonic Acid) and the various salts thereof, benzazolyl derivatives.

8. The composition according to claim 1, in which the water-soluble screening agents that are capable of absorbing UV rays from 280 to 320 nm (UVB) are chosen from water-soluble para-aminobenzoic compounds, cinnamic derivatives, salicylic compounds, benzylidenecamphor compounds and phenylbenzimidazole compounds.

9. The composition according to claim 1, in which the water-soluble screening agents that are capable of absorbing UV rays from 280 to 320 nm (UVB) is 2-phenyl-1H-benzimidazole-5-sulfonic acid (INCI name: Phenylbenzimidazolesulfonic acid).

10. The composition according to claim 1, comprising a total amount of water-soluble or water-dispersible screening agents of between 2% and 10% by weight relative to the total weight of the composition.

11. The composition according to claim 1, in which the at least one hydrophilic thickener is chosen from anionic synthetic thickening polymers, nonionic thickening polysaccharides, sulfate-based thickening polysaccharides and carboxylic branched thickening polysaccharides.

12. The composition according to claim 11, in which the anionic synthetic thickening polymers are chosen from crosslinked homopolymers or copolymers of acrylic or methacrylic acid, crosslinked or non-crosslinked 2-acrylamido-2-methylpropanesulfonic acid homopolymers, or salts thereof, and copolymers of acrylamido-2-methylpropanesulfonic acid or salts thereof and of one or more crosslinked or non-crosslinked nonionic monomers, alone or as mixtures.

13. The composition according to claim 11, in which the anionic synthetic thickening polymers are chosen from crosslinked acrylic acid homopolymers.

14. The composition according to claim 11, in which the anionic synthetic thickening polymers are chosen from crosslinked copolymers of (meth)acrylic acid and of a C1-C30 alkyl acrylate.

15. The composition according to claim 11, in which the anionic synthetic thickening polymers are chosen from copolymers of acrylamido-2-methylpropanesulfonic acid or salts thereof and of one or more nonionic monomers.

16. The composition according to claim 11, in which the copolymers of acrylamido-2-methylpropanesulfonic acid or salts thereof and of one or more nonionic monomers are chosen from copolymers of acrylamido-2-methylpropanesulfonic acid and of vinylpyrrolidone, crosslinked acrylamide/sodium acrylamido-2-methylpropanesulfonate copolymers, copolymers of acrylamido-2-methylpropanesulfonic acid and of hydroxyethyl acrylate and hydrophobically modified copolymers of acrylamido-2-methylpropanesulfonic acid.

17. The composition according to claim 11, in which the anionic synthetic thickening polymers are present in an amount ranging from 0.05% to 35% by weight, relative to the total weight of the composition.

18. The composition according to claim 11, in which the nonionic thickening polysaccharides are chosen from nonionic cellulose-based thickening polysaccharides.

19. The composition according to claim 11, in which the nonionic thickening polysaccharides are chosen from nonionic cellulose-based thickening polysaccharides and in which the sulfate-based thickening polysaccharides are chosen from sulfate-based polysaccharides.

20. The composition according to claim 11, in which the nonionic thickening polysaccharides are chosen from nonionic cellulose-based thickening polysaccharides and in which the carboxylic branched thickening polysaccharides are chosen from anionic branched polysaccharides based on glucose, mannose, acetylated mannose, pyruvic acid and glucuronic acid.

21. The composition according to claim 11, in which the nonionic thickening polysaccharides are chosen from nonionic cellulose-based thickening polysaccharides and in which the thickening polysaccharides are present in an amount ranging from 0.01% to 20% by weight relative to the total weight of the composition.

22. The composition according to claim 11, in which the at least one surfactant with an HLB of greater than or equal to 7 have an HLB of greater than 7 and less than 40.

23. The composition according to claim 11, in which the at least one surfactant with an HLB of greater than or equal to 7 is chosen from:

esters of a fatty acid;

water-soluble silicones including at least one terminal or pendent monovalent polyoxyalkylene group;

and mixtures thereof.

24. The composition according to claim 1, in which the at least one surfactant with an HLB of greater than or equal to 7 is present in concentrations ranging from 0.5% to 5% by weight relative to the total weight of the composition.

25. The composition according to claim 1, which does not include a screening agent in addition to the at least one screening agent.

26. The composition according to claim 1, having an amount of fatty phase of less than 2% by weight of the composition.

27. The composition according to claim 1, which does not contain a fatty phase.

28. The composition according to claim 1, which comprises between 2% and 25% by weight relative to the total weight of the composition of the at least one screening agent; from 2% to 10% by weight, relative to the total weight of the composition of the at least one hydrophilic thickener; and from 0.5% to 5% by weight relative to the total weight of the composition of the at least one surfactant with an HLB of greater than or equal to 7.

29. A non-therapeutic cosmetic process for treating a keratin material comprising the application to the keratin material of a composition according to claim 1.

* * * * *